United States Patent
Jensen et al.

(10) Patent No.: US 8,483,800 B2
(45) Date of Patent: *Jul. 9, 2013

(54) SURGICAL NAVIGATION ENABLED IMAGING TABLE ENVIRONMENT

(75) Inventors: Vernon Thomas Jensen, Draper, UT (US); William H. Huber, Scotia, NY (US)

(73) Assignee: General Electric Company, Schenectady, NY (US)

( * ) Notice: Subject to any disclaimer, the term of this patent is extended or adjusted under 35 U.S.C. 154(b) by 678 days.

This patent is subject to a terminal disclaimer.

(21) Appl. No.: 12/325,197

(22) Filed: Nov. 29, 2008

(65) Prior Publication Data

US 2010/0138183 A1 Jun. 3, 2010

(51) Int. Cl.
A61B 5/05 (2006.01)
G01R 33/02 (2006.01)
G01R 33/00 (2006.01)

(52) U.S. Cl.
USPC ............ 600/424; 324/252; 324/226; 702/150

(58) Field of Classification Search
USPC ..................... 600/424–427; 73/779; 324/226, 324/252; 702/150; 9/424–427
See application file for complete search history.

(56) References Cited

U.S. PATENT DOCUMENTS

| | | | |
|---|---|---|---|
| 5,396,905 A | 3/1995 | Newman et al. | |
| 5,422,621 A * | 6/1995 | Gambino et al. | ........... 338/32 R |
| 5,729,129 A | 3/1998 | Acker | |
| 5,752,513 A | 5/1998 | Acker et al. | |
| 5,782,765 A | 7/1998 | Jonkman | |
| 5,818,323 A * | 10/1998 | Maeda et al. | ............... 338/32 R |
| 6,161,032 A * | 12/2000 | Acker | ........................... 600/424 |
| 6,172,499 B1 | 1/2001 | Ashe | |
| 6,211,666 B1 * | 4/2001 | Acker | ...................... 324/207.17 |
| 6,241,671 B1 | 6/2001 | Ritter et al. | |
| 6,246,231 B1 | 6/2001 | Ashe | |
| 6,366,799 B1 * | 4/2002 | Acker et al. | .................. 600/424 |
| 6,381,485 B1 | 4/2002 | Hunter et al. | |
| 6,427,079 B1 | 7/2002 | Schneider et al. | |
| 6,493,573 B1 | 12/2002 | Martinelli et al. | |
| 6,528,991 B2 | 3/2003 | Ashe | |
| 6,610,602 B2 * | 8/2003 | Gambino et al. | ............. 438/689 |

(Continued)

FOREIGN PATENT DOCUMENTS

| | | |
|---|---|---|
| EP | 42707 | 12/1981 |
| JP | 2002365010 | 12/2002 |
| WO | WO9732179 | 9/1997 |
| WO | WO9960370 | 11/1999 |

OTHER PUBLICATIONS

"Introduction to Materials Science & Engineering, Chapter 18. Electrical Properties" May 8, 2007 pp. 9-11.<http://bp.snu.ac.kr/Lecture/materials_science%5C%EA%B0%95%EC%9D%98%EC%9E%90% EB%A3%8C/MSE-18-Electrical%20Properties (70)-2007-05-08.pdf>.*

Primary Examiner — Lisa Caputo
Assistant Examiner — Jonathan Dunlap

(57) ABSTRACT

A system for integrating radiolucent tracking sensors in a medical table, table mat, or surgical drape of a surgical navigation system, allowing the surgical navigation system to be less obtrusive in a surgery environment. A plurality of radiolucent magnetoresistance sensors are integrated into a table, table mat, or surgical draping of a surgical navigation system for improving surgical navigation workflow and eliminating image artifacts from intraoperative images. The plurality of radiolucent magnetoresistance sensors may be located within a table or adjacent to a table surface.

15 Claims, 3 Drawing Sheets

U.S. PATENT DOCUMENTS

| | | |
|---|---|---|
| 6,618,612 B1 * | 9/2003 | Acker et al. ............ 600/424 |
| 6,636,757 B1 | 10/2003 | Jascob et al. |
| 6,642,714 B2 * | 11/2003 | Kobayashi et al. ............ 324/252 |
| 6,690,963 B2 * | 2/2004 | Ben-Haim et al. ............ 600/424 |
| 6,701,179 B1 | 3/2004 | Martinelli et al. |
| 6,714,374 B1 * | 3/2004 | Hayashi et al. ............ 360/66 |
| 6,784,660 B2 | 8/2004 | Ashe |
| 6,789,043 B1 | 9/2004 | Nelson et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,856,823 B2 | 2/2005 | Ashe |
| 7,174,202 B2 * | 2/2007 | Bladen et al. ............ 600/424 |
| 7,176,798 B2 | 2/2007 | Dimmer et al. |
| 7,195,645 B2 * | 3/2007 | Disilvestro et al. ............ 623/18.11 |
| 7,324,915 B2 * | 1/2008 | Altmann et al. ............ 702/150 |
| 7,373,271 B1 | 5/2008 | Schneider |
| 7,402,996 B2 | 7/2008 | Arai et al. |
| 7,683,612 B2 * | 3/2010 | Koyama ............ 324/249 |
| 8,283,921 B2 * | 10/2012 | Huber et al. ............ 324/252 |
| 2003/0011359 A1 | 1/2003 | Ashe |
| 2003/0173953 A1 | 9/2003 | Ashe |
| 2003/0233042 A1 | 12/2003 | Ashe |
| 2004/0068178 A1 * | 4/2004 | Govari ............ 600/424 |
| 2005/0047734 A1 * | 3/2005 | Borom ............ 385/98 |
| 2005/0245817 A1 * | 11/2005 | Clayton et al. ............ 600/424 |
| 2005/0245821 A1 * | 11/2005 | Govari et al. ............ 600/429 |
| 2005/0261566 A1 | 11/2005 | Hanley |
| 2006/0025668 A1 | 2/2006 | Peterson et al. |
| 2007/0078334 A1 | 4/2007 | Scully et al. |
| 2007/0121791 A1 * | 5/2007 | Haupl et al. ............ 378/206 |
| 2007/0167703 A1 * | 7/2007 | Sherman et al. ............ 600/407 |
| 2007/0191706 A1 * | 8/2007 | Calderon et al. ............ 600/415 |
| 2007/0232898 A1 * | 10/2007 | Huynh et al. ............ 600/424 |
| 2007/0233238 A1 * | 10/2007 | Huynh et al. ............ 623/2.11 |
| 2008/0001756 A1 | 1/2008 | Dimmer et al. |
| 2008/0269596 A1 | 10/2008 | Revie et al. |
| 2008/0312530 A1 * | 12/2008 | Malackowski et al. ............ 600/426 |
| 2009/0033742 A1 | 2/2009 | Jensen ............ 348/77 |
| 2009/0058413 A1 * | 3/2009 | Kraemer et al. ............ 324/252 |
| 2009/0105779 A1 * | 4/2009 | Moore et al. ............ 607/20 |
| 2009/0118620 A1 * | 5/2009 | Tgavalekos et al. ............ 600/463 |
| 2009/0143973 A1 * | 6/2009 | Litvin et al. ............ 701/200 |
| 2009/0281421 A1 * | 11/2009 | Culp et al. ............ 600/426 |
| 2010/0137705 A1 * | 6/2010 | Jensen et al. ............ 600/424 |
| 2010/0138183 A1 * | 6/2010 | Jensen et al. ............ 702/150 |
| 2010/0249571 A1 * | 9/2010 | Jensen et al. ............ 600/409 |
| 2010/0305427 A1 * | 12/2010 | Huber et al. ............ 600/424 |

* cited by examiner

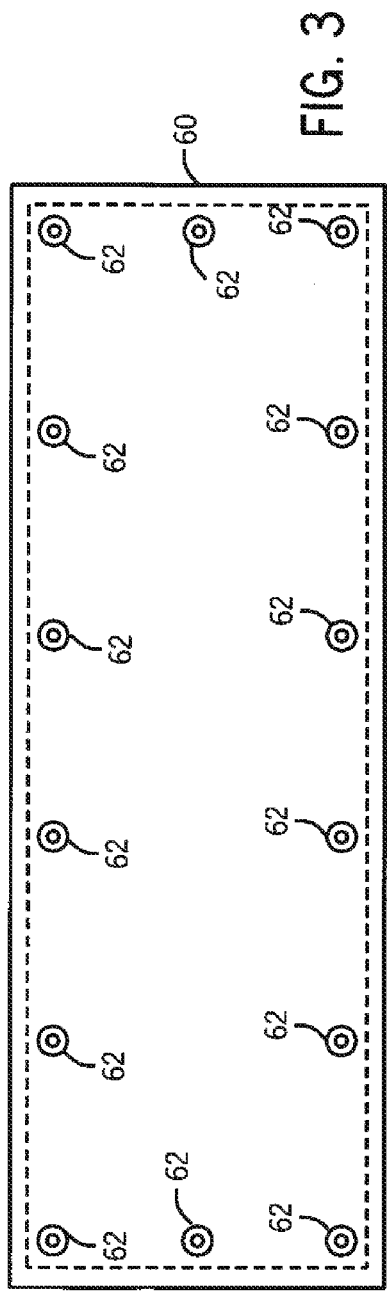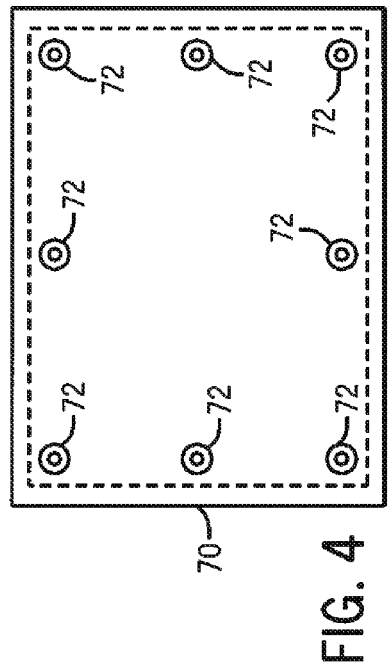

SURGICAL NAVIGATION ENABLED IMAGING TABLE ENVIRONMENT

BACKGROUND OF THE INVENTION

This disclosure relates generally to surgical navigation systems, and more particularly to a system for integrating radiolucent tracking sensors in a medical table.

Surgical navigation systems track the precise position and orientation of surgical instruments, implants or other medical devices in relation to multidimensional images of a patient's anatomy. Additionally, surgical navigation systems use visualization tools to provide the surgeon with co-registered views of these surgical instruments, implants or other medical devices with the patient's anatomy.

The multidimensional images may be generated either prior to (pre-operative) or during (intraoperative) the surgical procedure. For example, any suitable medical imaging technique, such as X-ray, computed tomography (CT), magnetic resonance (MR), positron emission tomography (PET), ultrasound, or any other suitable imaging technique, as well as any combinations thereof may be utilized. After registering the multidimensional images to the position and orientation of the patient, or to the position and orientation of an anatomical feature or region of interest, the combination of the multidimensional images with graphical representations of the navigated surgical instruments, implants or other medical devices provides position and orientation information that allows a medical practitioner to manipulate the surgical instruments, implants or other medical devices to desired positions and orientations.

Current surgical navigation systems that include position and orientation sensors, or sensing sub-systems based on electromagnetic (EM), radio frequency (RF), optical (line-of-sight), and/or mechanical technology.

Surgical navigation using these various technologies are used today with limited acceptance in various clinical applications where an x-ray compatible medical table is used. The navigation area is determined by the proximity of the navigation sensors relative to the position of the patient, medical devices and imaging apparatus. A major reason for the limited acceptance of surgical navigation during medical procedures is related to changes required in the normal surgical workflow that complicates the set-up, execution and turn-around time in the operating room. Most navigation enabled medical devices and environments also add mechanical and visual obstructions within the surgical region of interest and the imaging field of view.

Sensors of known navigation systems are not radiolucent, and if left in the imaging field of view will cause unwanted x-ray image artifacts. This is true with radiographic imaging, but it is of greater concern with intraoperative fluoroscopic 2D and 3D imaging. Based on common constraints across various navigation clinical applications, where intraoperative x-ray imaging is used, the most important region of interest for the navigation system is shared with the most important region of interest for the imaging system. Obvious preferred locations for sensors are not only in the imaging region of interest, but include the area above, below and even within the medical table itself.

EM and RF based navigation sensors have advantages over optical sensors in an intraoperative imaging environment (range, accuracy, non line-of-site), however, the composition of the medical table itself (carbon fiber) can introduce magnetic field distortions that can limit the use of these sensor technologies in some clinical applications.

Previous competitive surgical navigation system designs are stand alone systems that do not attempt to integrate non-radiolucent navigation sensors into the imaging environment. If placed in the x-ray image field of view, the non-radiolucent sensors create distracting image artifacts.

Therefore, there is a need for a surgical navigation system that integrates radiolucent sensors into the medical table environment for simplifying surgical workflow, eliminating distortion, and eliminating image artifacts.

BRIEF DESCRIPTION OF THE INVENTION

In accordance with an aspect of the disclosure, a surgical navigation system comprising at least one magnetoresistance sensor attached to at least one device; a plurality of magnetoresistance sensors integrated within a surgical navigation table environment; and at least one processor for determining the position and orientation of the at least one device.

In accordance with an aspect of the disclosure, a surgical navigation system comprising at least one magnetoresistance sensor attached to at least one device; a magnetoresistance reference sensor rigidly attached to an anatomical reference of a patient; a plurality of magnetoresistance sensors integrated within a table or located adjacent to a surface of the table; and at least one processor for determining the position and orientation of the at least one device.

In accordance with an aspect of the disclosure, a medical table with embedded tracking technology for use in a surgical navigation system, the medical table comprising a plurality of magnetoresistance sensors integrated within the table; wherein each of the plurality of magnetoresistance sensors are radiolucent.

Various other features, aspects, and advantages will be made apparent to those skilled in the art from the accompanying drawings and detailed description thereof.

BRIEF DESCRIPTION OF THE DRAWINGS

FIG. 3 is a schematic diagram of an exemplary embodiment of a medical table embedded with magnetoresistance sensors; and FIG. 4 is a schematic diagram of an exemplary embodiment of a surgical drape embedded with magnetoresistance sensors.

DETAILED DESCRIPTION OF THE INVENTION

Figure 1:
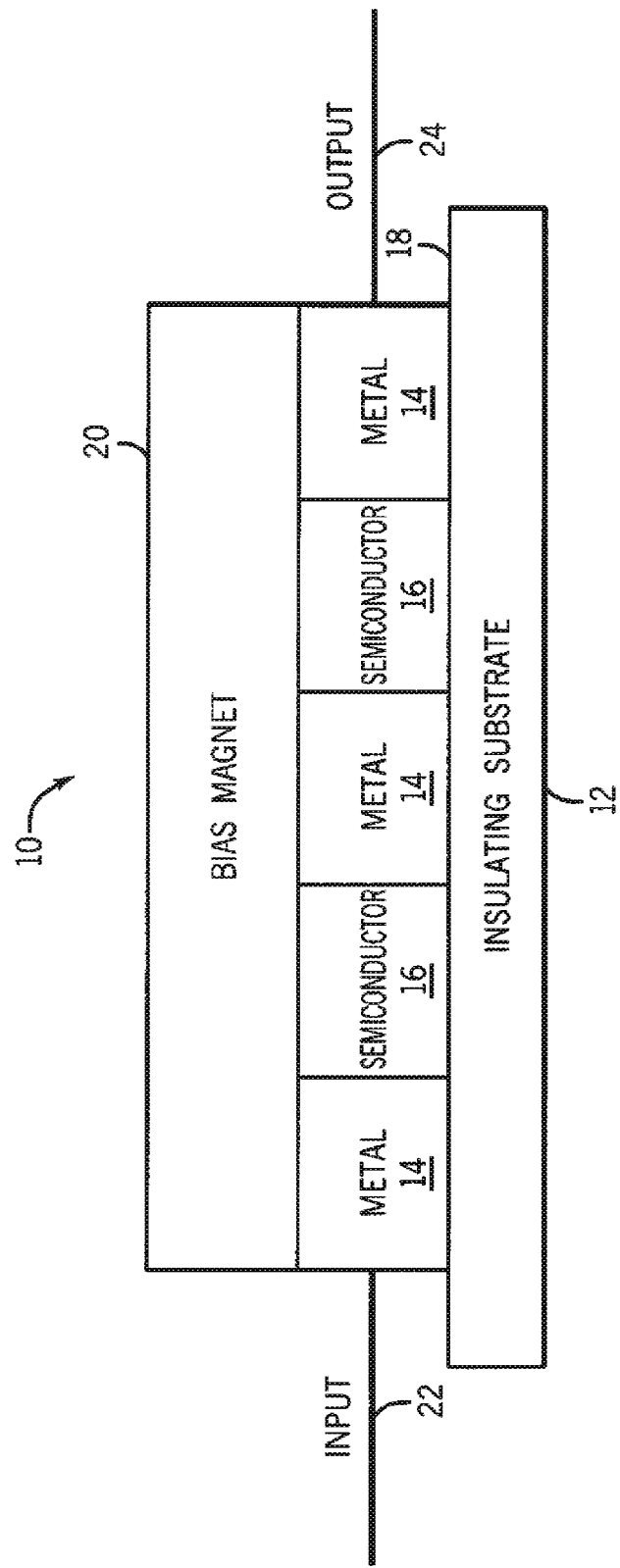
FIG. 1 is an enlarged side view of an exemplary embodiment of a magnetoresistance sensor.

Referring now to the drawings, FIG. 1 illustrates an enlarged side view of an exemplary embodiment of a magnetoresistance sensor 10. A magnetoresistance device is a device that provides a change in electrical resistance of a conductor or semiconductor when a magnetic field is applied. The device's resistance depends upon the magnetic field applied. As shown in FIG. 1, the a magnetoresistance sensor 10 comprises an insulating substrate 12, an alternating pattern of a metal material 14 and a semiconductor material 16 deposited on a surface 18 of the insulating substrate, and a bias magnet material 20 deposited over the alternating pattern of metal material 14 and semiconductor material 16. The alternating pattern of metal material 14 and semiconductor material 16 creates a composite structure with alternating bands of metal material 14 and semiconductor material 16. At least one input connection contact 22 is coupled to the metal material 14 and at least one output connection contact 24 is coupled to the metal material 14. The magnetoresistance sensor 10 is radiolucent.

The semiconductor material 16 may be series connected to increase the magnetoresistance sensor 10 resistance. In an exemplary embodiment, the semiconductor material 16 may be comprised of a single semiconductor element. The bias magnet material 20 subjects the semiconductor material 16 to a magnetic field required to achieve required sensitivity. The magnetoresistance sensor 10 provides a signal in response to the strength and direction of a magnetic field. In an exemplary embodiment, the magnetic field may be approximately 0.1 to 0.2 Tesla.

The application of a magnetic field confines the electrons to the semiconductor material 16, resulting in an increased path length. Increasing the path length, increases the sensitivity of the magnetoresistance sensor 10. The magnetic field also increases the resistance of the magnetoresistance sensor 10. In the geometry disclosed in FIG. 1, at a zero magnetic field, the current density is uniform throughout the magnetoresistance sensor 10. At a high magnetic field, the electrons (or holes) propagate radially outward toward the corners of the semiconductor material 16, resulting in a large magnetoresistance (high resistance).

Many new clinical applications include tracking of a variety of devices including catheters, guidewires, and other endovascular instruments that require sensors to be very small in size (millimeter dimensions or smaller). The active area of the magnetoresistance sensor 10 may be scaled to sizes less than 0.1 mm×0.1 mm.

In an exemplary embodiment, the magnetoresistance sensor may be built with various architectures and geometries, including, giant magnetoresistance (GMR) sensors, and extraordinary magnetoresistance (EMR) sensors.

The magnetoresistance sensor 10 provides a very small form factor, excellent signal-to-noise ratio (low noise operation), and excellent low frequency response. Low noise combined with wide dynamic range enables the magnetoresistance sensor 10 to be used for position and orientation tracking in surgical navigation systems. The low frequency response of the magnetoresistance sensor 10 allows a surgical navigation system to operate at very low frequencies where metal tolerance is maximized.

Figure 2:
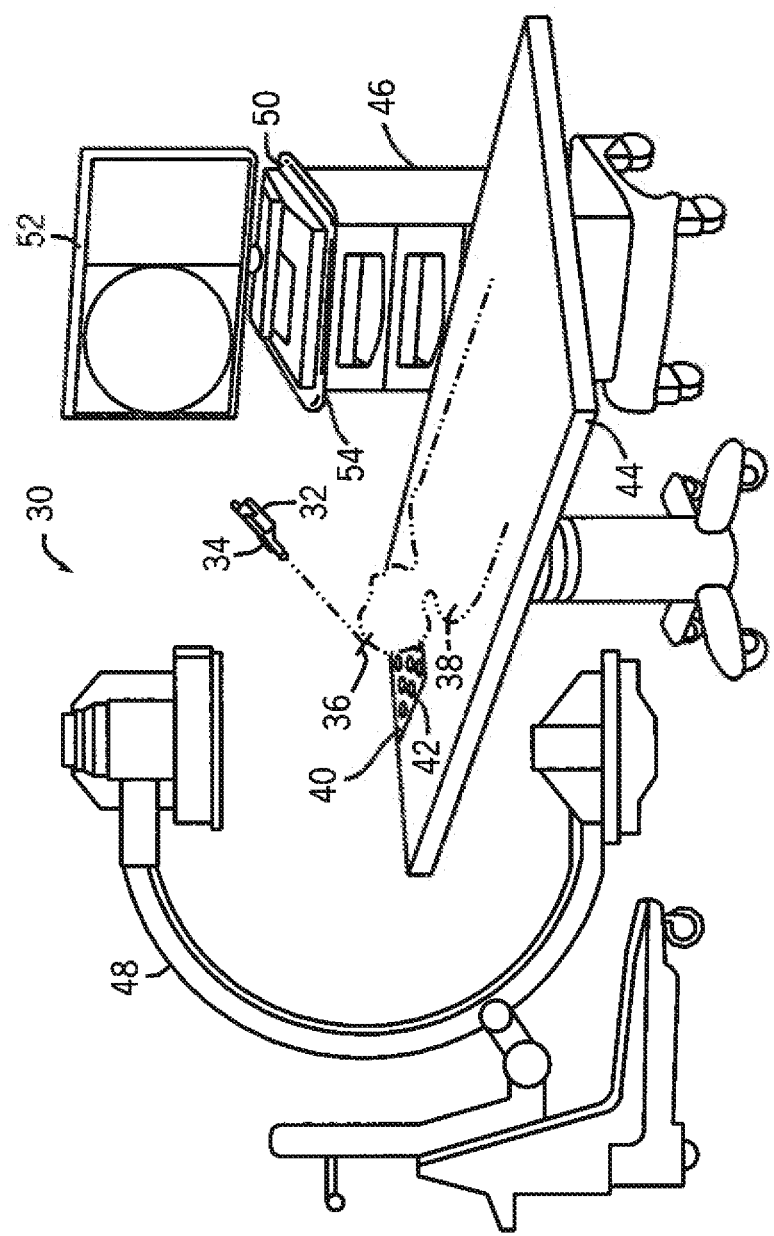
FIG. 2 is a schematic diagram of an exemplary embodiment of a surgical navigation system.

FIG. 2 illustrates a schematic diagram of an exemplary embodiment of a surgical navigation system 30. The surgical navigation system 30 includes at least one magnetoresistance sensor 32 attached to at least one device 34, a magnetoresistance reference sensor 36 rigidly attached to an anatomical reference of a patient 38 undergoing a medical procedure, a plurality of magnetoresistance sensors 42 integrated within a table mat 40 positioned on a table 44 supporting the patient 38, an imaging apparatus 48, and a portable workstation 46. In an exemplary embodiment, the imaging apparatus 48 is a mobile fluoroscopic imaging apparatus. The portable workstation 46 includes a computer 50, at least one display 52, and a navigation interface 54. The surgical navigation system 30 is configured to operate with the at least one magnetoresistance sensor 32, the magnetoresistance reference sensor 36, and the plurality of magnetoresistance sensors integrated in the table mat 40 to determine the position and orientation of the at least one device 34. The table mat 40 and plurality of magnetoresistance sensors 42 integrated therein are radiolucent. In an exemplary embodiment, the table mat 40 may be a single use or multiple use disposable product.

The at least one magnetoresistance sensor 32 may be used to determine one dimension or multiple dimensions of position and/or orientation information (x, y, z, roll, pitch, yaw) relative to the at least one magnetoresistance reference sensor 36, or relative to plurality of magnetoresistance sensors 42 integrated within a table mat 40. The at least one magnetoresistance sensor 32 is movable with respect to the magnetoresistance reference sensor 36 and the plurality of magnetoresistance sensors 42 for determining the position and orientation of the at least one magnetoresistance sensor 32 relative to the at least one magnetoresistance reference sensor 36, or relative to plurality of magnetoresistance sensors 42 integrated within a table mat 40.

In an exemplary embodiment, the plurality of magnetoresistance sensors 42 may be configured in an array of magnetoresistance sensors 42 integrated within the table mat 40.

The at least one magnetoresistance sensor 32, the magnetoresistance reference sensor 36, and the plurality of magnetoresistance sensors 42 are coupled to the navigation interface 54. The at least one magnetoresistance sensor 32, the magnetoresistance reference sensor 36, and the plurality of magnetoresistance sensors 42 may be coupled to and communicate to the navigation interface 54 through either a wired or wireless connection. The navigation interface is coupled to the computer 50.

The at least one magnetoresistance sensor 32 communicates with and transmits and/or receives data from the magnetoresistance reference sensor 36, and the plurality of magnetoresistance sensors 42. The navigation interface 54 is coupled to and transmits/receives data from the at least one magnetoresistance sensor 32, communicates with and transmits/receives data from the magnetoresistance reference sensor 36, and communicates with and transmits/receives data from the plurality of magnetoresistance sensors 42. The surgical navigation system 30 provides the ability to track and display the position and orientation of at least one device 34 having at least one magnetoresistance sensors 32 attached thereto. The position and orientation information may be transmitted from the computer 50 to the display 52 for review by a medical practitioner.

In an exemplary embodiment, the at least one magnetoresistance sensor 32 may be configured as a transmitter or magnetic field generator, the magnetoresistance reference sensor 36 may be configured as a transmitter or magnetic field generator, and the plurality of magnetoresistance sensors 42 may be configured as magnetic field receivers. In this embodiment, the at least one magnetoresistance sensor 32 and the magnetoresistance reference sensor 36 generate at least two different magnetic fields that are detected by the plurality of magnetoresistance sensors 42 (magnetic field measurements).

In an exemplary embodiment, the at least one magnetoresistance sensor 32 may be configured as a magnetic field receiver, the magnetoresistance reference sensor 36 may be configured as a magnetic field receiver, and the plurality of magnetoresistance sensors 42 may be configured as transmitters or magnetic field generators for creating a volume of magnetic fields that encompass a portion or substantially all of the table 44 and the patient 38. The device 34 maybe moved relative to the table 44, table mat 40 and the plurality of magnetoresistance sensors 42 within the volume of magnetic fields. In this embodiment, the plurality of magnetoresistance sensors 42 generate a plurality of different magnetic fields that are detected by the at least one magnetoresistance sensor 32 and the magnetoresistance reference sensor 36 (magnetic field measurements).

Theses magnetic field measurements may be used to calculate the position and orientation of the at least one device 34 according to any suitable method or system. After the magnetic field measurements are digitized using electronics coupled to the at least one magnetoresistance sensor 32, the digitized signals are transmitted from the at least one magnetoresistance sensor 32 to the navigation interface 46. The digitized signals may be transmitted from the at least one magnetoresistance sensor 32 to the navigation interface 46 using wired or wireless communication protocols and interfaces. The digitized signals received by the navigation interface 46 represent magnetic field information detected by the at least one magnetoresistance sensor 32 or the plurality of magnetoresistance sensors 42.

In an exemplary embodiment, the digitized signals received by the navigation interface 46 represent magnetic field information from the at least one magnetoresistance reference sensor 34 detected by the plurality of magnetoresistance sensors 42 or the at least one magnetoresistance sensor 32 and the magnetoresistance reference sensor 36. The navigation interface 46 transfers the digitized signals to the computer 42. The computer 42 calculates position and orientation information of the at least one device 34 based on the received digitized signals. The position and orientation information may be transmitted from the computer 50 to the display 52 for review by a medical practitioner.

The surgical navigation system 30 described herein is capable of tracking many different types of devices during different procedures. Depending on the procedure, the at least one device 34 may be a surgical instrument (e.g., an imaging catheter, a diagnostic catheter, a therapeutic catheter, a guidewire, a debrider, an aspirator, a handle, a guide, etc.), a surgical implant (e.g., an artificial disk, a bone screw, a shunt, a pedicle screw, a plate, an intramedullary rod, etc.), or some other device. Depending on the context of the usage of the surgical navigation system 30, any number of suitable devices may be used. In an exemplary embodiment, there may be more than one device 34, and more than one magnetoresistance sensor 32 attached to each device 34.

In an exemplary embodiment, a magnetoresistance reference sensor is fixed to an anatomical reference, a first magnetoresistance sensor is attached to a first device or implant, and a second magnetoresistance sensor is fixed to a second device, implant or imaging apparatus.

In an exemplary embodiment, a magnetoresistance sensor is integrated within or around a surgical table, a magnetoresistance reference sensor is fixed to an anatomical reference, and a plurality of magnetoresistance sensors are fixed to devices, implants, patient body parts, and/or an imaging apparatus.

In an exemplary embodiment, the table 44 may include, for example, an operating room table, an x-ray imaging table, a combination operating and imaging table, or a Jackson table, generally used for spine and orthopedic applications. In addition, table 44 may include any other medical apparatus that could benefit from tracking technology, including, for example, an imaging apparatus useful in x-ray examinations of patients.

An exemplary system for implementing the computer 42 may include a general purpose computing device including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic bard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

FIG. 3 illustrates a schematic diagram of an exemplary embodiment of a medical table 60 with a plurality of magnetoresistance sensors 62 integrated therein. The medical table 60 may be used with the surgical navigation system 30 of FIG. 2 by replacing the table mat 40 and table 44 with medical table 60. The plurality of magnetoresistance sensors 62 may be integrated into the table 60 in any suitable pattern. The plurality of magnetoresistance sensors 62 integrated into the table 60 are radiolucent.

As described above, by embedding the plurality of magnetoresistance sensors 62 into table 60, the sensors 62 become fixed with respect to the table 60. In this way, magnetic field distortions normally caused by table 60 may be corrected by creating a magnetic field map at the time the table 60 is manufactured. In contrast, by not integrating a plurality of magnetoresistance sensors 62 into a table 60, any magnetic field distortion caused by the table 60 must either be accounted for by creating a distortion-free table or by mapping the magnetic field before each and every use.

In an exemplary embodiment, the plurality of magnetoresistance sensors 62 may be configured in an array of magnetoresistance sensors 62 integrated within the table 60.

FIG. 4 illustrates a schematic diagram of an exemplary embodiment of a surgical drape 70 with a plurality of magnetoresistance sensors 62 integrated therein. The surgical drape 70. The surgical drape 70 may be used with the surgical navigation system 30 of FIG. 2. The plurality of magnetoresistance sensors 62 may be integrated into the surgical drape 70 in any suitable pattern. The surgical drape 70 may be placed over the table 44 or over the patient 38 during a medical procedure. The surgical drape 70 includes a plurality of magnetoresistance sensors 72 integrated therein. The plurality of magnetoresistance sensors 72 may be integrated into the table 70 in any suitable pattern. The surgical drape 70 may be a single use or multiple use disposable product. The plurality of magnetoresistance sensors 72 integrated into the surgical drape 70 are radiolucent.

In an exemplary embodiment, the plurality of magnetoresistance sensors 72 may be configured in an array of magnetoresistance sensors 72 integrated within the surgical drape 70.

In an exemplary embodiment, the magnetoresistance sensors integrated into the surgical navigation table environment provide for low distortion, distortion compensation, or distortion free operation in this environment (low frequency, multi-frequency, and coil free).

In an exemplary embodiment, a system for integrating radiolucent tracking sensors in a medical table, table mat, or surgical drape of a surgical navigation system, allowing the surgical navigation system to be less obtrusive in a surgery environment. Today, stand-alone surgical navigation systems take-up valuable operating room space, and require time consuming set-up and take down time.

In an exemplary embodiment, a plurality of radiolucent magnetoresistance sensors are integrated into a table, table mat, or surgical draping of a surgical navigation system for improving surgical navigation workflow and eliminating image artifacts from intraoperative images. The plurality of radiolucent magnetoresistance sensors may be located within a table or adjacent to a table surface.

In an exemplary embodiment, where a portion of a medical device is visible in intraoperative images, it may be removed or subtracted out of the image by using a pre-acquired mask image using known device geometry and position and orientation information.

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A surgical navigation system comprising:
   at least one magnetoresistance sensor attachable to at least one device;
   a plurality of magnetoresistance sensors integrated within a table or adjacent to a surface of the table; and
   at least one processor for determining the position and orientation of the at least one device;
   wherein the at least one magnetoresistance sensor attachable to the at least one device and the plurality of magnetoresistance sensors integrated within the table each comprising:
   an insulating substrate;
   an alternating pattern of a metal material and a semiconductor material deposited on a surface of the insulating substrate; and
   a bias magnet material deposited on a surface of the alternating pattern of the metal material and the semiconductor material; and
   wherein the alternating pattern of the metal material and the semiconductor material is between the insulating substrate and the bias magnet material.

2. The surgical navigation system of claim 1, wherein the plurality of magnetoresistance sensors are integrated within a table.

3. The surgical navigation system of claim 2, wherein the table is radiolucent.

4. The surgical navigation system of claim 1, wherein the plurality of magnetoresistance sensors are integrated within a table mat positioned adjacent to the surface of the table.

5. The surgical navigation system of claim 4, wherein the table mat is radiolucent.

6. The surgical navigation system of claim 1, wherein the plurality of magnetoresistance sensors are integrated within a surgical drape positioned over a patient.

7. The surgical navigation system of claim 6, wherein the surgical drape is radiolucent.

8. The medical table of claim 1, wherein each of the plurality of the magnetoresistance sensors have an active area of 0.1 mm by 0.1 mm.

9. A surgical navigation system comprising:
   at least one magnetoresistance sensor attachable to at least one device;
   a magnetoresistance reference sensor rigidly attachable to an anatomical reference of a patient;
   a plurality of magnetoresistance sensors integrated within a table or located adjacent to a surface of the table; and
   at least one processor for determining the position and orientation of the at least one device;
   wherein the at least one magnetoresistance sensor attachable to the at least one device and the plurality of magnetoresistance sensors integrated within the surgical navigation table each comprising:
   an insulating substrate;
   an alternating pattern of a metal material and a semiconductor material deposited on a surface of the insulating substrate; and
   a bias magnet material deposited on a surface of the alternating pattern of the metal material and the semiconductor material; and
   wherein the alternating pattern of the metal material and the semiconductor material is between the insulating substrate and the bias magnet material.

10. The surgical navigation system of claim 9, wherein the plurality of magnetoresistance sensors are integrated within a table mat positioned adjacent to the surface of the table.

11. The surgical navigation system of claim 10, wherein the table mat is radiolucent.

12. The surgical navigation system of claim 9, wherein the plurality of magnetoresistance sensors are integrated within a surgical drape positioned over a patient.

13. The surgical navigation system of claim 12, wherein the surgical drape is radiolucent.

14. The surgical navigation system of claim 9, wherein the table is radiolucent.

15. A medical table with embedded tracking technology for use in a surgical navigation system, the medical table comprising:
   a plurality of magnetoresistance sensors integrated within the medical table;
   wherein each of the plurality of magnetoresistance sensors comprising:
   an insulating substrate;
   an alternating pattern of a metal material and a semiconductor material deposited on a surface of the insulating substrate; and
   a bias magnet material deposited on a surface of the alternating pattern of the metal material and the semiconductor material; and
   wherein the alternating pattern of the metal material and the semiconductor material is between the insulating substrate and the bias magnet material.

* * * * *